United States Patent
Raspet

(10) Patent No.: US 11,352,618 B2
(45) Date of Patent: Jun. 7, 2022

(54) MODIFIED ORGANISMS FOR IMPROVED FLAVOR AND AROMA

(71) Applicant: Sean Raspet, Detroit, MI (US)

(72) Inventor: Sean Raspet, Detroit, MI (US)

(*) Notice: Subject to any disclaimer, the term of this patent is extended or adjusted under 35 U.S.C. 154(b) by 412 days.

(21) Appl. No.: 16/383,086

(22) Filed: Apr. 12, 2019

(65) Prior Publication Data

US 2019/0292534 A1  Sep. 26, 2019

Related U.S. Application Data

(60) Provisional application No. 62/647,410, filed on Mar. 23, 2018.

(51) Int. Cl.
| | | |
|---|---|---|
| *C12N 15/10* | (2006.01) | |
| *C12N 15/90* | (2006.01) | |
| *C12N 9/00* | (2006.01) | |
| *C12N 9/06* | (2006.01) | |
| *C12N 9/10* | (2006.01) | |
| *C12N 9/88* | (2006.01) | |

(52) U.S. Cl.
CPC ......... *C12N 15/102* (2013.01); *C12N 15/902* (2013.01); *C12N 2310/20* (2017.05); *C12N 2800/80* (2013.01)

(58) Field of Classification Search
None
See application file for complete search history.

(56) References Cited

U.S. PATENT DOCUMENTS 8,535,883 B2 * 9/2013 Cane .................. C12Q 1/689
435/6.1
2016/0272980 A1  9/2016 Duchateau et al.

FOREIGN PATENT DOCUMENTS

EP  0567433 B1  10/1996
WO  2015017866 A1  2/2015

OTHER PUBLICATIONS

Yang Ou, et al., "Activation of SAT 1 Engages Polyamine Metabolism with p53-mediated Ferroptotic Responses," PNAS, Date: Oct. 3, 2016, pp. E6806-E6812.
International Search Report and Written Opinion, dated Jul. 11, 2019, for corresponding PCT Application No. PCT/US2019/027322, International Filing Date Apr. 12, 2019, consisting of 5 pages.

* cited by examiner

*Primary Examiner* — Suzanne M Noakes
*Assistant Examiner* — Jae W Lee
(74) *Attorney, Agent, or Firm* — Gearhart Law LLC; David Postolski, Esq.

(57) ABSTRACT

The present disclosure provides for genetically modified organisms that provide numerous health benefits but also have an improved flavor profile and a more palatable aroma for the consumer of the organism.

2 Claims, No Drawings

MODIFIED ORGANISMS FOR IMPROVED FLAVOR AND AROMA

CLAIM OF PRIORITY

This application claims priority to U.S. Application 62/657,410 filed on Apr. 13, 2018, the contents of which are herein fully incorporated by reference in its entirety.

FIELD OF THE EMBODIMENTS

The field of the embodiments of the present invention relate to genetically modified organisms, namely algae, to impart an improved flavor and/or aroma to the organism.

BACKGROUND OF THE EMBODIMENTS

Presently, there's an ever-growing need for additional food sources, particularly food sources that are inexpensive to produce and nutritious. Moreover, the global reliance on meat products, as the staple of many diets, contributes significantly to the release of greenhouse gases. Thus, there is a need for new foodstuffs that are palatable and nutritious while also being ecologically efficient with a low greenhouse gas footprint.

Algae have long been looked to as a potential source of food. While certain types of algae, primarily seaweed, do indeed provide important foodstuffs for human consumption, the promise of algae as a foodstuff has not yet been fully realized. However, there are several species of algae that are used in foodstuffs today, most being macroalgae such as kelp, dulse and sea lettuce. Microalgae, such as *Spirulina*, are grown commercially in open ponds or tanks for use as a nutritional supplement or incorporated in small amounts in various beverages. Other microalgae, including some species of *chlorella*, are also utilized as a nutritional supplement. Microalgae are potentially easier to cultivate and much more resource efficient than macroalgae, producing much more biomass with the same amount of inputs. Despite the use of microalgae in supplements, they have not been widely adopted as a staple food source.

The above described algal uses do have drawbacks. For example, algal powders made with algae grown photosynthetically in outdoor ponds or photobioreactors are readily available but have a deep green color and a characteristic unpleasant taste. When formulated into food products or as nutritional supplements, these algal powders impart an unpleasant fishy, muddy, or seaweed-like flavor and odor.

Thus, there remains a need for to produce foodstuffs from algae cheaply and efficiently, at large scale, that are both tasty and nutritious. Such modification may be accomplished via genetic modification of the organism. The present invention and its embodiments meet these and other needs.

SUMMARY OF THE EMBODIMENTS

The present invention relates to a platform that can be used to genetically modify a target genome in a plant or an algae or in another organism to make the organism more palatable. In one instance, the platform includes a CRISPR/Cas system (e.g., a type I, II, or III CRISPR/Cas system, as well as modified versions thereof, such as a CRISPR/dCas9 system), TALENs, or zinc fingers to accomplish the desired genomic editing.

Some have endeavored to grow various organisms in media having additional nitrogen or copper or a combination thereof to remove/reduce the presence of any of the compounds listed herein and other compounds not explicitly listed herein. While growing conditions and the fertilizer/nutrient profile can alter the flavor of the organism, it also reduces the flexibility of producers to optimize their growth conditions towards efficiency and nutrition. The present invention and its embodiments makes a highly-targeted alteration to the organism to remove the source of the specific flavor volatiles, without requiring any large scale infrastructural or process changes.

In one embodiment of the present invention there is a method of genetic modification of an organism, the method comprising: identifying at least one genomic location of the organism, wherein the at least one genomic location corresponds to genes that code for an enzyme such as: a geosmin synthase gene, a germacradienol synthase gene, a MIB synthase gene, or 2-MIB synthase gene or 2-methylisoborneol synthase gene, a 2-pentylfuran synthase gene, a spermidine synthase gene, a spermine synthase gene, a thermospermine synthase gene, a diamine oxidase gene, lipases, lipoxygenases, agmatine imino hydroxylase, arginine decarboxylase, lysine decarboxylase, ahistamineN-methyltransferase gene, another gene related to polyamine production, a beta-ionone synthase gene, or any combination thereof; and editing the at least one genomic location of the organism by knocking out the at least one genomic location or in the alternative, upregulating or downregulating the at least one genomic location.

In yet another embodiment of the present invention there is a method of producing a better tasting organism comprising: editing a genome of the organism to target production of at least one of the following molecules: geosmin, 2-methylisoborneol, 2-pentylfuran, putrescine, cadaverine, spermine, spermindine, thermospermine, and polyamines having a molecular weight below 350 Daltons.

In one embodiment of the present invention the organism is algae. In one embodiment of the present invention, the editing step, as described herein, is performed by CRISPR, TALENs, or zinc fingers.

DESCRIPTION OF THE PREFERRED EMBODIMENTS

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

In general, the present invention and its embodiments provide an algal food product for human consumption that is rich in nutrients with a satisfying taste. *Spirulina* (*Arthrospira platensis*) is an economically useful algae cyanobacteria that contains a high level of beneficial nutrients and protein that also has an expedient growth rate. This makes *spirulina* a sustainable and healthy food source. Despite these benefits, the flavor of *spirulina* and other algae has prevented it from widespread consumer adoption. The present application identified herein sources of the undesirable flavors associated with *spirulina* and other algae. In particular, *spirulina* produces several molecules that relate to several perceived off notes from the consumer perspective. Two potent off-note molecules are geosmin and 2-methylisoborneol and other off notes include 2-pentylfuran and di-amino compounds such as cadaverine, putrescine, spermidine, spermine, thermospermine and others.

Genome editing (also called gene editing) is a group of technologies that provide the ability to change an organism's DNA. These technologies allow genetic material to be added, removed, or altered (upregulated, downregulated, etc.) at particular locations in the genome. Several approaches to genome editing have been developed and are becoming widely utilized. One approach is known as CRISPR-Cas9. The CRISPR-Cas9 system is faster, cheaper, more accurate, and more efficient than other previously-existing genome editing methods.

Further, engineered zinc finger arrays may be utilized to modify an organism's DNA. Engineered zinc finger arrays are often fused to a DNA cleavage domain to generate zinc finger nucleases thereby creating useful reagents for manipulating genomes of various organisms. For example, by targeting a double-strand break to a desired genomic locus one can introduce frame-shift mutations into the coding sequence of a gene. If a homologous DNA "donor sequence" is also used, then the targeted genomic locus can be converted to a defined DNA sequence via the homology directed repair pathway.

Similarly, TALENs can be used to edit genomes by inducing double-strand breaks to which cells respond to with repair mechanisms. TALENs are simply restriction enzymes that can be engineered to cut specific sequences of DNA thereby allowing potential negative genes to be excised from the genome. One advantage of TALENs is that these restriction enzymes can be engineered to bind to practically any DNA sequence.

The present invention and its embodiments are directed to utilizing the above and other genomic editing techniques to remove unwanted traits, particularly aroma and taste, from various organisms. For example, geosmin (shown below) is an organic compound that imparts an earthy, muddy flavor and aroma into organisms in which it is produced. Particularly, problematic is that the human nose is extremely sensitive to geosmin and is able to detect it at concentrations as low as 5 parts per trillion (the human nose is responsible for most of a food's flavor via retronasal olfaction). The human nose can often detect it at thresholds below that of standard GCMS analysis.

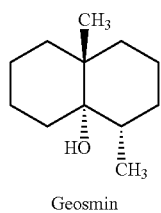

Geosmin

Another compound, 2-methylisoborneol or 2-MIB (shown below), is an organic compound that gives off an unpleasant earthy odor. Many blue-green algae produce 2-MIB and geosmin which results in an undesirable odor and taste that is imparted to the blue-green algae and other 2-MIB containing organisms.

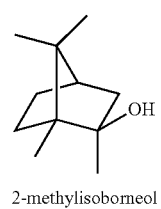

2-methylisoborneol

Other compounds include the class of polyamines, including several volatile diamino compounds such as putrescine and cadaverine, among others. These compounds can impart a fishy, fleshy and even fowl aroma and flavor. Larger polyamine molecules tend to have a less potent smell, therefore, one embodiment of the invention upregulates the genes for enzymes that convert smaller polyamines into larger polyamines, thus decreasing the proportion of smaller polyamines in the organism. Another embodiment down-regulates the production of polyamines in order to reduce their overall concentration.

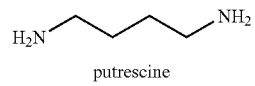

putrescine

The above compounds are intended to be exemplary only and other compounds, including but not limited to Beta-cyclocitral, 1-octen-3-ol, Sulfides (including dimethyl sulfide and dimethyl trisulfide), Thiomethyl esters, and 2,4-decadienal, 1,3-Octadiene, Octatrienes, 4-Methylthio-1,2-dithiolane, 5-Methylthio-1,2,3-trithiane, Dimethyldisulfide, Dimethyltrisulfide, Methyl ethanethiolate, Methyl propanethiolate, Methyl 2-methy 1propanethiolate, Methyl 3-methylbutanethiolate, Pentanal, Heptanal, Dimethyltetrasulfide, 1,2,4-Trithiolane, Oct-1-en-3-o-1, Octan-1-ol, Oct-2-en-1-ol, 1-octen-3-one, Octan-3-one, Benzene, Naphthalene, Hexanal, Pentan-3-one, Styrene, Octanal, Decanal, Nonanal, Undecanal, histamine, Thioesters, Uric acids, Uronic acids, Purines, Pinene, Limonene, Borneol, Fenchol, Indole, Skatole, Polyunsaturated fatty acids, and Free fatty acids may be targeted through the genomic editing processes described herein to obtain a more palatable organism.

In a preferred embodiment, the organism is a microalgae. More preferably, the microalgae is a species selected from the group consisting of *Arthrospira platensis*, *Arthrospira maxima*, the genus *Arthrospira*, *Chlorella vulgaris*, the genus *Chlorella*, the division *Chlorophyta*, *Chlamydomonas reinhardtii*, *Dunaliella salina*, the genus *Euglena*, *Nannochloropsis occulate*, the genus *Nannochloropsis*, *Haematococcus pluvialis*, the genus *Ulva*, the genus *Enteromorpha*, the genus *Spirulina*, "red algae", "brown algae", "green algae", "blue-green algae", *Parachlorella kessleri*, *Parachlorella beijerinckii*, *Neochloris oleabundans*, *Bracteacoccus*, including *B. grandis*, *B. cinnabarinas*, and *B. aerius*, *Bracteococcus* sp. or *Scenedesmus rebescens*. Other nonlimiting examples of microalgae species include those species from the group of species and genera consisting of *Achnanthes orientalis*; *Agmenellum*; *Amphiprora hyaline*; *Amphora*, including *A. coffeiformis* including *A.c. linea*, *A.c. punctata*, *A.c. taylori*, *A.c. tenuis*, *A.c. delicatissima*, *A.c. delicatissima capitata*; *Anabaena*; *Ankistrodesmus*, including *A. falcatus*; *Aphanizomenon flosaquae*; *Bacillariophyceae*; *Boekelovia hooglandii*; *Borodinella*; *Botryococcus braunii*, including *B. sudeticus*; *Bracteoccocus*, including *B. aerius*, *B. grandis*, *B. cinnabarinas*, *B. minor*, and *B. medionucleatus*; *Carteria*; *Chaetoceros*, including *C. gracilis*, *C. muelleri*, and *C. muelleri subsalsum*; *Chlorococcum*, including *C. infusionum*; *Chlorogonium*; *Chlorophyceae*; *Chlorophyta*; *Chroomonas*; *Chrysosphaera*; *Chrysophyceae*; *Cricosphaera*; *Crypthecodinium cohnii*; *Cryptomonas*; *Cryptophyceae*; *Cyclotella*, including *C. cryptica* and *C. meneghiniana*; *Cyanophyceae*; *Cyanobacteria*; *Dunaliella*, including *D. bardawil*, *D. bioculata*, *D. granulate*, *D. maritime*, *D. minuta*, *D. parva*, *D. peircei*, *D.*

*primolecta, D. salina, D. terricola, D. tertiolecta*, and *D. viridis; Dinophyceae; Eremosphaera*, including *E. viridis; Ellipsoidon; Euglenozoa; Franceia; Fragilaria*, including *F. crotonensis; Gleocapsa; Gloeothamnion; Hymenomonas; Isochrysis*, including *I. aff. galbana* and *I. galbana; Lepocinclis; Micractinium* (including UTEX LB 2614); *Monoraphidium*, including *M. minutum; Monoraphidium; Nannochloris; Nannochloropsis*, including *N. salina; Navicula*, including *N. acceptata, N. biskanterae, N. pseudotenelloides, N. pelliculosa*, and *N. saprophila; Neochloris oleabundans; Nephrochloris; Nephroselmis; Nitschia communis; Nitzschia*, including *N. alexandrina, N. communis, N. dissipata, N. frustulum, N. hantzschiana, N. inconspicua, N. intermedia, N. microcephala, N. pusilla, N. pusilla elliptica, N. pusilla monoensis*, and *N. quadrangular; Ochromonas; Oocystis*, including *O. parva* and *O. pusilla; Oscillatoria*, including *O. limnetica* and *O. subbrevis; Parachlorella*, including *P. beijerinckii* (including strain SAG 2046) and *P. kessleri* (including any of SAG strains 11.80, 14.82, 21.11H9); *Pascheria*, including *P. acidophila; Pavlova; Phagus; Phormidium; Platymonas; Pleurochrysis*, including *P. carterae* and *P. dentate; Prototheca*, including *P. stagnora* (including UTEX 327), *P. portoricensis*, and *P. moriformis* (including UTEX strains 1441, 1435, 1436, 1437, 1439); *Pseudochlorella aquatica; Pyramimonas; Pyrobotrys; Rhodococcus opacus; Rhodophyceae; Sarcinoid chrysophyte; Scenedesmus*, including *S. armatus* and *S. rubescens; Schizochytrium; Spirogyra; Spirulina platensis; Stichococcus; Synechococcus; Tetraedron; Tetraselmis*, including *T. suecica; Thalassiosira weissflogii*; and *Viridiella fridericiana*. In a preferred embodiment the algae is *spirulina (Arthrospira platensis)*. Various combinations of the aforementioned algae and other not specifically named herein may further be utilized under the purview of the present invention.

In other embodiments, algae (and other organisms) with removed genes such as those that code for enzymes responsible for the production of geosmin, 2-methylisoborneol, and 2-pentylfuran, and other molecules described herein will also improve the flavor of animals that consume algae including farmed salmon, cows, and chickens that use algae or algae containing food stuffs as feed. Further, the principles of the present invention and its embodiments will also be useful for cellular agriculture/cultured meat applications as an off-flavor free feedstock. Additionally, other applications of the techniques described herein could include altering the flavor profile of nitrogen fixing species of bacteria or cyanobacteria such that they can be used as fertilizer without imparting a muddy taste to the organism grown with the aid of the fertilizer.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method of genetic modification of an organism to produce a better tasting organism, the method comprising: identifying at least one genomic location of the organism, wherein the at least one genomic location corresponds to a geosmin synthase gene, a germacradienol synthase gene, methylisoborneol (MIB) synthase gene or 2-MIB synthase gene, 2-pentylfuran synthase gene or 2-pentylfuran producing gene, spermidine synthase gene, spermine synthase gene, theospermine synthase gene, diamine oxidase gene, histamine N-methyltransferase gene, beta-ionone synthase gene, a dimethylsulfoniopropionate lyase gene wherein the encoded enzyme produces dimethyl sulfide and dimethyl trisulfide, or any combination thereof, and editing the at least one genomic location of the organism by knocking out or making non-functional at least one genomic location or in the alternative, upregulating or downregulating the at least one genomic location to remove unwanted traits from the organism, wherein the unwanted traits comprise aroma and taste, and wherein the organism is algae.

2. The method of claim 1, wherein the editing step is performed using a CRISPR system, TALENs, or zinc fingers.

\* \* \* \* \*